US008828955B2

(12) United States Patent
Ohto et al.

(10) Patent No.: US 8,828,955 B2
(45) Date of Patent: Sep. 9, 2014

(54) GLUTATHIONE PRODUCTION ENHANCER, PROPHYLACTIC/THERAPEUTIC AGENT FOR DISEASES CAUSED BY GLUTATHIONE DEFICIENCY, AND FOOD, BEVERAGE AND FEED

(75) Inventors: Nobuaki Ohto, Fukuyama (JP); Toshiyuki Murakami, Fukuyama (JP); Hirokazu Ohno, Fukuyama (JP)

(73) Assignee: Maruzen Pharmaceuticals Co., Ltd., Hiroshima (JP)

( * ) Notice: Subject to any disclaimer, the term of this patent is extended or adjusted under 35 U.S.C. 154(b) by 428 days.

(21) Appl. No.: 12/991,199

(22) PCT Filed: May 1, 2009

(86) PCT No.: PCT/JP2009/058586
§ 371 (c)(1),
(2), (4) Date: Jan. 11, 2011

(87) PCT Pub. No.: WO2009/136611
PCT Pub. Date: Nov. 12, 2009

(65) Prior Publication Data
US 2011/0118201 A1 May 19, 2011

(30) Foreign Application Priority Data

May 9, 2008 (JP) ................................ 2008-123941

(51) Int. Cl.
| | | |
|---|---|---|
| A61K 31/704 | (2006.01) |
| A61K 31/7034 | (2006.01) |
| A61K 31/7028 | (2006.01) |
| C07H 15/24 | (2006.01) |
| C07H 15/20 | (2006.01) |
| A61K 31/7048 | (2006.01) |
| A23L 1/30 | (2006.01) |
| A23K 1/16 | (2006.01) |
| A61K 31/12 | (2006.01) |
| A61K 31/382 | (2006.01) |
| A61K 36/484 | (2006.01) |

(52) U.S. Cl.
CPC ........... *A61K 36/484* (2013.01); *A61K 31/7048* (2013.01); *A23L 1/3002* (2013.01); *A23K 1/1618* (2013.01); *A23K 1/1609* (2013.01); *A61K 31/12* (2013.01); *A61K 31/7034* (2013.01); *A61K 31/382* (2013.01)
USPC .................. 514/33; 514/35; 514/25; 536/4.1

(58) Field of Classification Search
USPC .................................. 514/35, 25, 33; 536/4.1
See application file for complete search history.

(56) References Cited

FOREIGN PATENT DOCUMENTS

| | | |
|---|---|---|
| JP | 04-009336 A | 1/1992 |
| JP | 04-082835 A | 3/1992 |
| JP | 2002-114695 A | 4/2002 |
| JP | 2003-081744 A | 3/2003 |
| JP | 2003-252784 A | 9/2003 |
| JP | 2006-111545 A | 4/2006 |
| JP | 2006-206513 A | 8/2006 |
| JP | 2006-241062 A | 9/2006 |
| JP | 2006-347934 A | 12/2006 |
| WO | WO 03/032966 | 4/2003 |
| WO | WO 03/084556 A1 | 10/2003 |

OTHER PUBLICATIONS

Li et al. (J Am Soc Mass Spectrom 2007, 18, 778-782).*
Trisha Gura; Sicience vol. 278, Nov. 7, 1997, pp. 1041-1042.*
Nordiske Seminar-og Arbejdsrapporter 1993:526, pp. 1-32.*
Yu, X.Q., et al., "In vitro and in vivo neuroprotective effect and mechanisms of glabridin, a major active isoflavan from *Glycyrrhiza glabra* (licorice)," *Life Sciences*, Jan. 2, 2008, vol. 82, No. 1-2, pp. 68-78.
International Search Report mailed on Jun. 2, 2009 for the corresponding International patent application No. PCT/JP2009/058586 (English translation enclosed).

* cited by examiner

*Primary Examiner* — Shaojia Anna Jiang
*Assistant Examiner* — Michael C Henry
(74) *Attorney, Agent, or Firm* — Posz Law Group, PLC

(57) ABSTRACT

The invention aims at finding a highly-safe natural product having glutathione production-enhancing activity, and providing a glutathione production enhancer and a prophylactic/therapeutic agent for diseases caused by glutathione deficiency using that natural product as an active ingredient. The glutathione production enhancer or the prophylactic/therapeutic agent for diseases caused by glutathione deficiency contains, as an active ingredient, a licorice extract composition that contains liquiritin, liquiritigenin, isoliquiritin and isoliquiritigenin but contains substantially no glycyrrhizic acid.

3 Claims, No Drawings

GLUTATHIONE PRODUCTION ENHANCER, PROPHYLACTIC/THERAPEUTIC AGENT FOR DISEASES CAUSED BY GLUTATHIONE DEFICIENCY, AND FOOD, BEVERAGE AND FEED

TECHNICAL FIELD

The present invention relates to a glutathione production enhancer, prophylactic/therapeutic agent for diseases caused by glutathione deficiency, and food, beverage and feed.

BACKGROUND ART

Glutathione is a tripeptide comprising three amino acids, namely glutamic acid, cysteine and glycine, and is a major cysteine residue-containing compound in cells. As is known, glutathione plays various roles in cells, for instance contributing to radical scavenging, redox-mediated regulation of cell function, and detoxifying mechanisms, as well as serving as a SH-donor for various enzymes.

Decreases in the intra-cellular concentration of glutathione that plays these roles are known to give rise to conditions such as cell damage due to ultraviolet radiation exposure, inflammation, blackening, formation of freckles and blemishes, acute or chronic alcohol-derived liver damage, liver disease, chronic renal failure, lung diseases caused by smoking, idiopathic pulmonary fibrosis, cataracts, ischemic heart disease, Parkinson's disease, Alzheimer's disease, gastric ulcer, adult respiratory syndrome, immunodeficiency, bone-marrow aplasia, acquired immunodeficiency syndrome, latent viral infections, aging phenomena derived from physiological aging, as well as oncogenesis. Conventional approaches to treat conditions caused by low concentration of glutathione in cells have involved using glutathione formulations that contain glutathione, with a view to eliciting uptake of glutathione by cells having a lowered intracellular glutathione concentration (Patent Document 1). However, therapy relying on oral ingestion of glutathione formulations may fail to elicit the anticipated effects, depending on the affected area to be treated. Although arguably more effective than oral ingestion, therapies by intravenous injection of glutathione formulations were problematic in that, for instance, injection is painful, and requires hospital visits.

Therefore, an increase in the intracellular glutathione concentration through promotion of glutathione production of cells in vivo should conceivably allow increasing defenses against oxidative stress, which decline with age, suppressing damage from oxidative stress caused by ultraviolet radiation, and preventing, treating or improving various diseases that include, for instance, skin aging, pigmentation disorders such as blemishes, and preventing and/or treating various organ dysfunctions and various diseases caused by glutathione deficiency. Known extraction products based on the above concept and having glutathione production-enhancing activity include, for instance, bilberry extraction products and walnut extraction products (Patent document 2), and extraction products of plants of the genus Gardenia (Patent document 3).

Glutathione is present in the organism in the form of reduced glutathione, which has the effect of removing reactive oxygen species, and oxidized glutathione, which is formed through reaction of reduced glutathione and reactive oxygen species. In recent years it has been found that oxidized glutathione is a sleep-promoting substance that promotes sleep by inhibiting neuronal excitability. Therefore, promoting glutathione production and increasing intracellular concentration, not only of reduced glutathione but also of oxidized glutathione, should conceivably be effective for preventing, treating or improving sleep disorders such as insomnia. Known sleep-inducing agents based on this concept include agents using oxidized glutathione as an active ingredient (Patent document 4).

In living cells, γ-glutamylcysteine is biosynthesized through reaction of glutamic acid and cysteine, mediated by γ-glutamylcysteine synthetase. As is known, glutathione is biosynthesized through reaction of γ-glutamylcysteine and glycine, mediated by glutathione synthetase. Therefore, the glutathione concentration of cells in vivo could be conceivably increased by promoting the expression of γ-glutamylcysteine synthetase, which acts as a catalyst in the biosynthesis of γ-glutamylcysteine as the precursor of glutathione.

Patent document 1: WO 2003/032966
Patent document 2: JP 2006-241062 A
Patent document 3: JP 2006-347934 A
Patent document 4: JP 4-9336 A

DISCLOSURE OF THE INVENTION

It is an object of the present invention to find highly-safe natural products having glutathione production-enhancing activity and γ-glutamylcysteine synthetase mRNA expression promotion activity, and to provide a glutathione production enhancer, prophylactic/therapeutic agent for diseases caused by glutathione deficiency, food and beverage, and feed, that have that natural product as an active ingredient.

In order to solve the above problem, a glutathione production enhancer and a prophylactic/therapeutic agent for diseases caused by glutathione deficiency of the present invention comprise, as an active ingredient, a licorice extract composition that contains liquiritin, liquiritigenin, isoliquiritin and isoliquiritigenin but contains substantially no glycyrrhizic acid.

A food and beverage and a feed of the present invention, comprise a licorice extract composition that contains liquiritin, liquiritigenin, isoliquiritin and isoliquiritigenin but contains substantially no glycyrrhizic acid.

Further, a method for promoting glutathione production in human cells in vivo or animal cells in vivo, of the present invention comprises administering, to a predetermined site of a human or an animal, a glutathione production enhancer containing a licorice extract composition that contains liquiritin, liquiritigenin, isoliquiritin and isoliquiritigenin but contains substantially no glycyrrhizic acid.

Further, a method for manufacturing a licorice extract composition that contains liquiritin, liquiritigenin, isoliquiritin and isoliquiritigenin but contains substantially no glycyrrhizic acid of the present invention comprises substantially removing glycyrrhizic acid from a licorice extract.

In the present invention, the term "containing substantially no glycyrrhizic acid" means that the glycyrrhizic acid content in the licorice extract composition is preferably no greater than 1.0 wt %, more preferably no greater than 0.5 wt %.

In the present invention, the term "licorice extract" means a liquid extracted using licorice as an extract raw material, a diluted or concentrated liquid of the liquid extract, or a dry product obtained by drying the liquid extract, and from which glycyrrhizic acid is not substantially removed. The "licorice extract composition" means a composition from which glycyrrhizic acid is substantially removed, and that contains liquiritin, liquiritigenin, isoliquiritin and isoliquiritigenin.

The present invention allows providing a glutathione production enhancer, a prophylactic/therapeutic agent for diseases caused by glutathione deficiency, a food and beverage, and a feed having excellent safety and containing, as an active ingredient, a licorice extract composition that comprises liquiritin, liquiritigenin, isoliquiritin and isoliquiritigenin but substantially no glycyrrhizic acid.

BEST MODE FOR CARRYING OUT THE INVENTION

Embodiments of the present invention are explained below.

[Glutathione Production Enhancer, Prophylactic/Therapeutic Agent Diseases Caused by Glutathione Deficiency]

The glutathione production enhancer and the prophylactic/therapeutic agent for diseases caused by glutathione deficiency of the present embodiment contain, as an active ingredient, a licorice extract composition that contains liquiritin, liquiritigenin, isoliquiritin and isoliquiritigenin but contains substantially no glycyrrhizic acid (hereafter, simply "licorice extract composition").

The licorice extract composition containing liquiritin, liquiritigenin, isoliquiritin and isoliquiritigenin but containing substantially no glycyrrhizic acid can be obtained by removing glycyrrhizic acid from a licorice extract that can be obtained in accordance with methods ordinarily used in plant extraction processes.

Examples of licorice as the extract raw material include, for instance, various species such as *Glycyrrhiza glabra, Glycyrrhiza inflata, Glycyrrhiza uralensis, Glycyrrhiza aspera, Glycyrrhiza eurycarpa, Glycyrrhiza pallidiflora, Glycyrrhiza yunnanensis, Glycyrrhiza lepidota, Glycyrrhiza echinata, Glycyrrhiza acanthocarpa* or the like. Any licorice species from among the foregoing may be used as the extract raw material. In particular, *Glycyrrhiza glabra, Glycyrrhiza uralensis* or *Glycyrrhiza inflata* is preferably used as the extract raw material.

The constituent portion of licorice that can be used as the extract raw material may include, for instance, aerial portions such as leaves, branches, barks, trunks, stems, fruits or flowers; as well as roots, rhizomes, and mixtures of the foregoing, preferably roots or rhizomes.

The licorice extract can be obtained by drying licorice as the extract raw material, followed by extraction of the dried licorice, as-is or ground using a coarse crusher, in an extraction solvent. Drying may involve air drying or drying using an ordinarily employed dryer. As the extract raw material licorice may also be used, for instance, after having subjected to a pre-treatment, for instance defatting using a non-polar solvent such as hexane. A pre-treatment such as defatting or the like allows carrying out the plant extraction using a polar solvent yet more efficiently.

Preferably, a polar solvent such as water, a hydrophilic organic solvent or the like is used as the extraction solvent. The polar solvent is used singly or in combinations of two or more, and is used preferably at room temperature or a temperature not higher than the boiling point of the solvent.

Examples of water that can be used as the extraction solvent include, for instance, pure water, tap water, well water, mineral spring water, mineral water, hot-spring water, spring water and fresh water, as well as water resulting from treating the foregoing in various ways. Examples of water treatment process include, for instance, purification, heating, sterilization, filtration, deionization, osmotic adjustment, acidification, alkalinization, buffering and the like. Therefore, examples of water that can be used as the extraction solvent in the present embodiment include, for instance, purified water, hot water, deionized water, saline water, organic acid water, ammonia alkaline water, phosphate buffered solution, phosphate buffered salines or the like.

Examples of the hydrophilic organic solvent that can be used as the extraction solvent include, for instance, C1-C5 lower aliphatic alcohols such as methanol, ethanol, propyl alcohol and isopropyl alcohol; a lower aliphatic ketone such as acetone or methyl ethyl ketone; and C2-C5 polyhydric alcohols such as 1,3-butylene glycol, propylene glycol or glycerin.

If the extraction solvent is used in the form of a mixed liquid of two or more types of polar solvent, the mixing ratio of the foregoing can be adjusted appropriately. For instance, in a case where a mixed liquid of water and a lower aliphatic alcohol is used, the mixture comprises preferably 1 to 90 parts by volume of lower aliphatic alcohol with respect to 10 parts by volume of water; in a case where a mixed liquid of water and a lower aliphatic ketone is used, the mixture comprises preferably 1 to 40 parts by volume of lower aliphatic ketone with respect to 10 parts by volume of water; in a case where a mixed liquid of water and a polyhydric alcohol is used, the mixture comprises preferably 10 to 90 parts by volume of polyhydric alcohol with respect to 10 parts by volume of water.

The extraction process is not particularly limited, provided that the soluble component comprised in the extract raw material can be eluted by the extraction solvent, and thus the extraction process may be carried out in accordance with ordinary methods. For instance, the extract raw material is immersed in 5 to 15 volumes (weight ratio) of extraction solvent, and the soluble component is extracted at normal temperature or under reflux heating. The liquid extract can be obtained then by removing the extraction residue by filtering. A paste-like concentrate is obtained upon evaporating of the solvent off the obtained liquid extract. This concentrate is further dried to yield a dry product.

The liquid extract, the concentrate of the liquid extract, or the dry product of the liquid extract, obtained as described above, contain the flavonoids liquiritin, liquiritigenin, isoliquiritin and isoliquiritigenin, and also glycyrrhizic acid. Therefore, glycyrrhizic acid is removed from the liquid extract, the concentrate of the liquid extract, or the dry product (licorice extract) of the liquid extract.

To remove glycyrrhizic acid from the licorice extract, an 80 to 95 vol % alcohol-water solution is added to the licorice extract, the extraction product from the licorice is dispersed into the alcohol-water solution, and is then suction-filtered with filter paper. Glycyrrhizic acid is soluble in water but poorly soluble in alcohol. Therefore, glycyrrhizic acid comprised in the licorice extract virtually does not dissolve in the alcohol-water solution, and is removed as a precipitate. By contrast, liquiritin, liquiritigenin, isoliquiritin and isoliquiritigenin are soluble in alcohol, and dissolve readily in the alcohol-water solution.

The alcohol used as the dispersion medium is not particularly limited, and may be, for instance, a C1-C5 lower aliphatic alcohol such as methanol, ethanol, propyl alcohol or isopropyl alcohol.

Water is added to the residue formed by evaporating the solvent off the obtained filtrate, followed by column chromatography using a porous substance such as silica gel, alumina or the like, or a porous resin such as a styrene-divinylbenzene copolymer or polymethacrylate, with sequential elution with water and alcohol. A licorice extract composition is obtained thus in the form of the fraction eluted with alcohol, which contains liquiritin, liquiritigenin, isoliquiritin and isoliquiritigenin but contains substantially no glycyrrhizic acid.

The alcohol used as the eluent in column chromatography is not particularly limited, and may be, for instance, a C1-C5 lower aliphatic alcohol such as methanol, ethanol, propyl alcohol or isopropyl alcohol, or a solution of the foregoing in water.

The alcohol fraction obtained by column chromatography may be further purified in accordance with any organic compound purification method, for instance reverse-phase silica gel chromatography using ODS, recrystallization, liquid-liquid countercurrent extraction, or column chromatography using an ion-exchange resin.

Other than the above-described method, the methods described below may also be used for removing glycyrrhizic acid from a licorice extract and obtain thereby a licorice extract composition containing liquiritin, liquiritigenin, isoliquiritin and isoliquiritigenin but containing substantially no glycyrrhizic acid.

For instance, a mineral acid (such as sulfuric acid, nitric acid, hydrochloric acid or the like) is added to the licorice extract, to adjust pH from about 1.0 to 3.0, and elicit thereby acid precipitation. The obtained acid precipitation solution is filtered to recover the precipitate. To the latter there is added a 30 to 90 vol %, preferably 30 to 70 vol % alcohol-water solution (aqueous solution of a C1-C5 lower aliphatic alcohol such as methanol, ethanol, propyl alcohol or isopropyl alcohol), followed by filtering.

The pH of the filtrate thus obtained is adjusted to about 3.0 to 5.0, preferably about 3.0 to 3.5, using aqueous ammonia, to cause glycyrrhizic acid to precipitate, followed by solid-liquid separation. The obtained filtrate fraction is neutralized through addition of sodium carbonate. This is followed by column chromatography using a porous substance such as silica gel, alumina or the like, or a porous resin such as a styrene-divinylbenzene copolymer or polymethacrylate, with sequential elution with water and alcohol. A licorice extract composition is obtained thus in the form of the fraction eluted with alcohol, which contains liquiritin, liquiritigenin, isoliquiritin and isoliquiritigenin but contains substantially no glycyrrhizic acid. The alcohol used as the eluent in column chromatography may be the same as the above-described ones.

The alcohol fraction obtained by column chromatography may be further purified in accordance with any organic compound purification method, for instance reverse-phase silica gel chromatography using ODS, recrystallization, liquid-liquid countercurrent extraction, or column chromatography using an ion-exchange resin.

The licorice extract composition containing liquiritin, liquiritigenin, isoliquiritin and isoliquiritigenin but containing substantially no glycyrrhizic acid can be obtained by removing glycyrrhizic acid from the licorice extract, as described above. The content of glycyrrhizic acid, i.e. licorice extract composition is preferably no greater than 1.0 wt %, more preferably no greater than 0.5 wt %.

The licorice extract composition containing liquiritin, liquiritigenin, isoliquiritin and isoliquiritigenin but containing substantially no glycyrrhizic acid thus obtained has glutathione production-enhancing activity, and can therefore be used, thanks to that effect, as an active ingredient of a glutathione production enhancer. The licorice extract composition has also γ-glutamylcysteine synthetase mRNA expression promotion activity, and hence can be used, thanks to that effect, as an active ingredient of a γ-glutamylcysteine synthetase mRNA expression enhancer.

Thanks to its glutathione production-enhancing activity, the licorice extract composition can promote the production of glutathione, and therefore can be used as the active ingredient of a prophylactic/therapeutic agent for diseases caused by glutathione deficiency (for instance, diseases caused by oxidative stress from reactive oxygen species or the like; liver diseases such as hepatitis and liver dysfunction; chronic renal failure; respiratory diseases such as idiopathic pulmonary fibrosis or adult respiratory syndrome; cataracts; ischemic heart disease; Parkinson's disease; Alzheimer's disease; gastrointestinal diseases such as gastric ulcer; cancer; bone marrow aplasia; acquired immunodeficiency syndrome; latent viral infections and the like).

Further, the licorice extract composition has glutathione production-enhancing activity, and, thanks to that effect, allows raising the intracellular concentration of oxidized glutathione. Therefore, the licorice extract composition can also be used as an active ingredient in preventive, therapeutic or improving agents for sleep disorders such as insomnia.

The glutathione production enhancer or the prophylactic/therapeutic agent for diseases caused by glutathione deficiency of the present embodiment may comprise the licorice extract composition alone, or a preparation formulated with the licorice extract composition.

The licorice extract composition can be formulated any form, for instance in powder, granule, tablet or liquid form, according to ordinary methods, using pharmaceutically acceptable carriers such as dextrins, cyclodextrins or the like, and arbitrary auxiliary agents of the carriers. As such auxiliary agents there can be used, for instance, excipients, binders, disintegrating agents, lubricants, stabilizers, flavoring agents, odor-improving agents and the like. The licorice extract composition can be used blended with other compositions (for instance, food and beverages), and can also be used as an ointment, topical solution, adhesive patch or the like.

The glutathione production enhancer and the prophylactic/therapeutic agent for diseases caused by glutathione deficiency of the present embodiment can be used as an active ingredient, as the case may require, blended with for instance another natural extraction product having glutathione production-enhancing activity.

The method for administering the glutathione production enhancer or the prophylactic/therapeutic agent for diseases caused by glutathione deficiency of the present embodiment may involve, for instance, administration to a predetermined site of a human or an animal, ordinarily by transdermal administration, oral administration, intravenous administration or the like. A method appropriate for preventing or treating a disease of interest may be appropriately selected in accordance with the type of the disease. Preferably, in particular, the glutathione production enhancer or the prophylactic/therapeutic agent for diseases caused by glutathione deficiency is administered by transdermal or oral administration.

The administration amount of the glutathione production enhancer and the prophylactic/therapeutic agent for diseases caused by glutathione deficiency of the present embodiment may be dosed in accordance with, for instance, the type of disease, the severity thereof, individual patient differences, the administration method and the administration period. An effective amount of the glutathione production enhancer or the prophylactic/therapeutic agent for diseases caused by glutathione deficiency of the present embodiment may be administered in accordance with, for instance, the type and severity of the disease.

By virtue of the glutathione production-enhancing activity of the licorice extract composition, the glutathione production enhancer of the present embodiment allows increasing defenses against oxidative stress, which decline with age, allows suppressing damage from oxidative stress caused by ultraviolet radiation, and allows preventing, treating or improving various diseases that include, for instance, skin aging, pigmentation disorders such as blemishes, and various organ dysfunctions caused by glutathione deficiency. Besides the above applications, the glutathione production enhancer of the present embodiment can also be used in all relevant applications for exerting glutathione production-enhancing activity.

As explained in below-described examples, the licorice extract composition, in particular, can promote effectively production of glutathione in epidermal keratinocytes and dermal fibroblasts. The glutathione production enhancer containing the licorice extract composition can eliminate reactive oxygen species in epidermal keratinocytes and dermal fibroblasts, allows protecting epidermal keratinocytes and dermal fibroblasts against damage caused by oxidative stress, and as a result allows preventing effectively, for instance, skin aging.

Glutathione has the effect of inhibiting maturation of tyrosinase. Promoting the production of glutathione allows thus further inhibiting tyrosinase maturation, and allows inhibiting generation of melanin by melanocytes. As a result, the glutathione production enhancer containing the licorice extract composition allows promoting effectively glutathione production in melanocytes, and further inhibiting tyrosinase maturation. This allows preventing, as a result, skin pigmentation disorders, skin blackening, blemishes, freckles and the like.

The licorice extract composition promotes effectively glutathione production in hepatocytes. Therefore, the glutathione production enhancer containing the licorice extract composition allows preventing and/or treating effectively liver diseases caused by glutathione deficiency.

Thanks to the γ-glutamylcysteine synthetase mRNA expression promotion activity of the licorice extract composition, biosynthesis of γ-glutamylcysteine, which is a precursor of glutathione, can be promoted by incorporating the licorice extract composition into the γ-glutamylcysteine synthetase mRNA expression enhancer.

Thanks to the glutathione production-enhancing activity of the licorice extract composition, the prophylactic/therapeutic agent for diseases caused by glutathione deficiency of the present embodiment allows preventing and/or treating diseases caused by glutathione deficiency (for instance, diseases caused by oxidative stress from reactive oxygen species or the like; liver diseases such as hepatitis and liver dysfunction; chronic renal failure; respiratory diseases such as idiopathic pulmonary fibrosis or adult respiratory syndrome; cataracts; ischemic heart disease; Parkinson's disease; Alzheimer's disease; gastrointestinal diseases such as gastric ulcer; cancer; bone marrow aplasia; acquired immunodeficiency syndrome; latent viral infections and the like), and allows raising the intracellular concentration of oxidized glutathione, being as a result effective for preventing, treating or improving sleep disorders such as insomnia.

[Food and Beverage, Feed]

The food and beverage or feed of the present embodiment is blended with a licorice extract composition that contains liquiritin, liquiritigenin, isoliquiritin and isoliquiritigenin but contains substantially no glycyrrhizic acid.

The licorice extract composition has glutathione production-enhancing activity, and has proved not to be digested in the gastrointestinal tract of, for instance, humans, animals and fish. The licorice extract composition has also excellent safety, and can therefore be appropriately blended with any food or drink, such as general foods, health food, health-promoting food, dietary supplements and the like; animal feed such as poultry or livestock feed, fish feed for farmed fish or the like; as well as feed in the form of pet food such as cat food, dog food or the like. In this case, the licorice extract composition may be blended as-is into the food, beverage or feed. Alternatively, a glutathione production enhancer or prophylactic/therapeutic agent for diseases caused by glutathione deficiency, formulated with the licorice extract composition, may be blended into the food, beverage or feed.

When the licorice extract composition, the glutathione production enhancer or the prophylactic/therapeutic agent for diseases caused by glutathione deficiency are blended into a food or beverage, the blending amount of active ingredient in the food or beverage can be appropriately adjusted in accordance with, for instance, the intended use, sex, symptoms and the like. However, the daily ingestion amount of extraction product is preferably set so as to range from about 1 to 1000 mg per day for adults, in consideration of the ordinary ingestion amount of the food and beverage to which the above are added.

The blending proportion of the licorice extract composition, the glutathione production enhancer or the prophylactic/therapeutic agent for diseases caused by glutathione deficiency when the foregoing are blended into feed can be appropriately adjusted in accordance with, for instance, the target organism (poultry, livestock, farmed fish, or pets such as cats and dogs), the body weight, intended purpose and so forth, but ranges preferably from 0.0001 to 20.0 wt %, more preferably from 0.01 to 2.0 wt %, in consideration of the ordinary ingestion amount of the feed to which the above are added.

The food and beverage into which the licorice extract composition, the glutathione production enhancer or prophylactic/therapeutic agent for diseases caused by glutathione deficiency can be blended is not particularly limited, so long as the glutathione production-enhancing activity of the licorice extract composition is unimpeded.

Specifically, the licorice extract composition, the glutathione production enhancer or the prophylactic/therapeutic agent for diseases caused by glutathione deficiency can be blended into, for instance, beverages (including undiluted concentrates and powders for preparation) such as soft drinks, carbonated drinks, nutritional drinks, fruit drinks, fermented lactic drinks ; frozen desserts such as ice cream, ice sherbets, shaved ice or the like; noodles such as soba, udon, harusame, gyoza wraps, shumai wraps, Chinese noodles, instant noodles and the like; confectionery such as sweets, chewing gum, candy, gum, chocolate, confectionery tablets, snacks, biscuits, jelly, jam, cream, baked confectionery or the like; processed marine and livestock products such as fish paste, ham, sausage or the like; dairy products such as processed milk, fermented milk or the like; oil, fats and oil-fat processed foods such as salad oil, tempura oil, margarine, mayonnaise, shortenings, whipped cream, dressings and the like; seasonings such as sauces, dips or the like; soups, stews, salads, side dishes, pickles; health products and supplements in various forms; as well as tablets, capsules and tonic drinks. The licorice extract composition, the glutathione production enhancer or the prophylactic/therapeutic agent for diseases caused by glutathione deficiency can be concomitantly used with other auxiliary raw materials and additives used in the foregoing foods and beverages.

EXAMPLES

The present invention will be explained in more detail below by way of preparation examples, experimental examples and blending examples. However, the present invention is not limited to these examples in any way.

Preparation Example 1

Herein, 10 L of water were added to 10 kg of crushed chips of licorice (*Glycyrrhiza glabra*) rhizomes, and extraction was carried out under gentle stirring, followed by solid-liquid separation by decantation, to yield a liquid extract. The obtained liquid extract was concentrated under vacuum to a paste-like consistency, after which 10 volumes of a 70 vol % ethanol-water solution were added to the obtained concentrate, and the whole was dispersed using a stirrer. The dispersion was kept at 5° C. overnight, the resulting precipitate was removed by suction-filtering using filter paper, and the ethanol-water solution was evaporated from the filtrate under reduced pressure.

Water was added to the residue thus obtained, to a solids fraction of 5%, and the whole was passed, at SV=1, through a column packed with 10 L of a porous synthetic adsorption resin (Diaion HP-20, by Mitsubishi Chemical). The column was washed with 50 L of water, and then 50 L of an 80 vol % ethanol-water solution was applied to the column to elute the flavonoids. The eluates were collected, and were vacuum-distilled to vaporize the ethanol-water solution off. Thereafter, the distillation residue was vacuum-dried at 40° C. and was crushed, to yield 345 g of a yellow-brown powder (sample 1).

The obtained powder was analyzed by high performance liquid chromatography under the below-described conditions. The results were glycyrrhizic acid content 0.5 wt %, liquiritin content 4.2 wt %, isoliquiritin content 3.6 wt %, liquiritigenin content 2.5 wt %, isoliquiritigenin content 1.5 wt %.

<Liquid Chromatography Conditions>
Stationary phase: JAIGEL GS-310 (by Japan Analytical Industry)
Column diameter: 20 mm
Column length: 500 mm
Mobile phase flow rate: 5 mL/min
Detection: RI Preparation Example 2

Herein, 410 g of a yellow-brown powder (sample 2) were obtained in the same way as in Example 1, but in this case there were added 10 L of 3% aqueous ammonia to 10 kg of crushed chips of licorice (*Glycyrrhiza uralensis*) rhizomes. The obtained powder was analyzed by high performance liquid chromatography in the same way as in Example 1. The results were glycyrrhizic acid content 0.9 wt %, liquiritin content 5.5 wt %, isoliquiritin content 4.6 wt %, liquiritigenin content 3.9 wt %, isoliquiritigenin content 3.5 wt %.

Preparation Example 3

Herein, 10 L of water were added to 10 kg of crushed chips of licorice (*Glycyrrhiza inflata*) rhizomes, and extraction was carried out under gentle stirring, followed by solid-liquid separation by decantation, to yield a liquid extract. The pH of the obtained liquid extract was adjusted to 2 through addition of 50% sulfuric acid, under stirring, to carry out an acid precipitation treatment. The precipitate was filtered and collected. Water was added to the obtained precipitate, and the whole was dispersed under stirring and was left to stand, after which the supernatant was removed by decantation. The above operation was repeated to remove the sulfuric acid, after which a precipitate was obtained through filtering.

Next, 5 L of 90 vol % ethanol were added to the precipitate thus obtained, and the whole was dispersed through stirring for 1 hour at normal temperature, followed by suction-filtering using diatomaceous earth. Aqueous ammonia was added to the obtained filtrate to adjust the pH of the latter to 5. The whole was left to stand at 5° C. for 2 days, to precipitate the glycyrrhizic acid. Thereafter, solid-liquid separation was carried out by centrifugation. The ethanol in the filtrate fraction was removed by vacuum distillation, and the distillation residue was neutralized with sodium carbonate.

The neutralized solution thus obtained was passed, at SV=1, through a column packed with 5 L of a porous synthetic adsorption resin (Diaion HP-20, by Mitsubishi Chemical). The column was washed with 25 L of water, and then 25 L of a 90 vol % ethanol-water solution was applied to the column to elute the flavonoids. The eluates were collected, and were vacuum-distilled to vaporize the ethanol-water solution off. Thereafter, the distillation residue was vacuum-dried at 40° C. and was crushed, to yield 293 g of a yellow-brown powder (sample 3)

The obtained powder was analyzed by high performance liquid chromatography in the same way as in Example 1. The results were glycyrrhizic acid content 0.8 wt %, liquiritin content 3.5 wt %, isoliquiritin content 2.8 wt %, liquiritigenin content 2.5 wt %, isoliquiritigenin content 1.8 wt %.

Experimental Example 1

Test of Glutathione Production-Enhancing Activity in Epidermal Keratinocytes

The glutathione production-enhancing activity of the licorice extract compositions obtained as described above (samples 1 to 3) was tested as described below.

Normal human epidermal keratinocytes (NHEK) were cultured using a culture medium for long-term culture of normal human epidermal keratinocytes (EpiLife-KG2), after which the cells were collected by trypsinization. The collected cells were diluted with EpiLife-KG2, to a cell density of $1.0 \times 10^5$ cells/mL. Thereafter, a 48-well plate was seeded with 200 µL of cells per well, and the cells were incubated overnight.

After incubation, 200 µL of the sample solution dissolved in EpiLife-KG2 (samples 1 to 3, sample concentration as per Table 1 below) were added to each well, followed by incubation for 24 hours. Once incubation was over, the medium was removed from the wells, and each well was washed with 400 µL of PBS (−). The cells were then lysed using 150 µL of M-PER (by PIERCE).

Total glutathione was quantified using 100 µL of that lysate. Specifically, a 96-well plate was charged with 100 µL of dissolved cell liquid lysate, 50 µL of a 0.1 M phosphate buffer solution, 25 µL of 2 mM NADPH, and 25 µL of glutathione reductase (final concentration 17.5 unit/mL), with warming for 10 minutes at 37° C. Next, 25 µL of 10 mM 5,5'-dithiobis (2-nitrobenzoic acid) were added, and absorbance was measured until 5 minutes thereafter at a wavelength of 412 nm, to work out ΔOD/min. The total glutathione concentration was calculated on the basis of a calibration curve plotted using oxidized glutathione (by Wako Pure Chemical). The obtained values were corrected to amount of glutathione per total protein amount, and then the glutathione production promotion rate (%) was calculated on the basis of the formula below.

$$\text{Glutathione production promotion rate (\%)} = B/A \times 100$$

In the formula, A denotes "amount of glutathione per total protein amount in cells with no sample added (control)", and B denotes "amount of glutathione per total protein amount in cells with sample added".

The results are given in Table 1.

TABLE 1

| Sample | Sample concentration (μg/mL) | Glutathione production promotion rate (%) |
|---|---|---|
| 1 | 6.25 | 114.9 |
|   | 12.5 | 128.5 |
|   | 25 | 145.2 |
| 2 | 6.25 | 118.1 |
|   | 12.5 | 151.6 |
|   | 25 | 188.4 |
| 3 | 6.25 | 109.9 |
|   | 12.5 | 129.6 |
|   | 25 | 142.2 |

As Table 1 shows, it was found that the licorice extract compositions containing liquiritin, liquiritigenin, isoliquiritin and isoliquiritigenin but containing substantially no glycyrrhizic acid were able to effectively promote glutathione production in epidermal keratinocytes.

Experimental Example 2

Test of Glutathione Production-Enhancing Activity in Dermal Fibroblasts

The glutathione production-enhancing activity of the licorice extract compositions obtained above (samples 1 to 3) was tested on dermal fibroblasts as described below.

Normal human dermal fibroblasts (NB1RGB) were cultured using 10% FBS-containing α-MEM, after which the cells were collected by trypsinization. The collected cells were diluted with 10% FBS-containing α-MEM, to a cell density of $2.0 \times 10^5$ cells/mL. Thereafter, a 48-well plate was seeded with 200 μL of cells per well, and the cells were incubated overnight.

After incubation, 200 μL of sample solution dissolved in 1% FBS-containing D-MEM (samples 1 to 3, sample concentration as per Table 2 below) were added to each well, followed by incubation for 24 hours. Once incubation was over, the medium was removed from the wells, and each well was washed with 400 μL of PBS (−). The cells were then lysed using 150 μL of M-PER (by PIERCE).

Total glutathione was quantified using 100 μL of that lysate. Specifically, a 96-well plate was charged with 100 μL of dissolved cell liquid lysate, 50 μL of a 0.1 M phosphate buffer solution, 25 μL of 2 mM NADPH, and 25 μL of glutathione reductase (final concentration 17.5 unit/mL), with warming for 10 minutes at 37° C. Next, 25 μL of 10 mM 5,5'-dithiobis(2-nitrobenzoic acid) were added, and absorbance was measured until 5 minutes thereafter at a wavelength of 412 nm, to work out ΔOD/min. The total glutathione concentration was calculated on the basis of a calibration curve plotted using oxidized glutathione (by Wako Pure Chemical). The obtained values were corrected to amount of glutathione per total protein amount, and then the glutathione production promotion rate (%) was calculated on the basis of the formula below.

Glutathione production promotion rate (%) = $B/A \times 100$

In the formula, A denotes "amount of glutathione per total protein amount in cells with no sample added (control)", and B denotes "amount of glutathione per total protein amount in cells with sample added".

The results are given in Table 2.

TABLE 2

| Sample | Sample concentration (μg/mL) | Glutathione production promotion rate (%) |
|---|---|---|
| 1 | 6.25 | 104.3 |
|   | 25 | 109.4 |
|   | 50 | 159.9 |
| 2 | 6.25 | 106.1 |
|   | 25 | 121.8 |
|   | 50 | 173.8 |
| 3 | 6.25 | 102.9 |
|   | 25 | 114.3 |
|   | 50 | 147.2 |

As Table 2 shows, it was found that the licorice extract compositions containing liquiritin, liquiritigenin, isoliquiritin and isoliquiritigenin but containing substantially no glycyrrhizic acid were able to effectively promote glutathione production in dermal fibroblasts.

Experimental Example 3

Test of Glutathione Production-Enhancing Activity in B16 Melanoma Cells

The glutathione production-enhancing activity of the licorice extract compositions obtained above (samples 1 to 3) was tested on B16 melanoma cells as described below.

B16 melanoma cells were cultured using 10% FBS-containing D-MEM medium, after which the cells were collected by trypsinization. The collected cells were diluted with 10% FBS-containing D-MEM, to a cell density of $1.0 \times 10^5$ cells/mL. Thereafter, a 48-well plate was seeded with 200 μL of cells per well, and the cells were incubated overnight.

After incubation, 200 μL of sample solution dissolved in 1% FBS-containing D-MEM medium (samples 1 to 3, sample concentration as per Table 3 below) were added to each well, followed by incubation for 24 hours. Once incubation was over, the medium was removed from the wells, and each well was washed with 400 μL of PBS (−). The cells were then lysed using 150 μL of M-PER (by PIERCE).

Total glutathione was quantified using 100 μL of that lysate. Specifically, a 96-well plate was charged with 100 μL of dissolved cell liquid lysate, 50 μL of a 0.1 M phosphate buffer solution, 25 μL of 2 mM NADPH, and 25 μL of glutathione reductase (final concentration 17.5 unit/mL), with warming for 10 minutes at 37° C. Next, 25 μL of 10 mM 5,5'-dithiobis (2-nitrobenzoic acid) were added, and absorbance was measured until 5 minutes thereafter at a wavelength of 412 nm, to work out ΔOD/min. The total glutathione concentration was calculated on the basis of a calibration curve plotted using oxidized glutathione (by Wako Pure Chemical). The obtained values were corrected to amount of glutathione per total protein amount, and then the glutathione production promotion rate (%) was calculated on the basis of the formula below.

Glutathione production promotion rate (%) = $B/A \times 100$

In the formula, A denotes "amount of glutathione per total protein amount in cells with no sample added (control)", and B denotes "amount of glutathione per total protein amount in cells with sample added".

The results are given in Table 3.

TABLE 3

| Sample | Sample concentration (µg/mL) | Glutathione production promotion rate (%) |
|---|---|---|
| 1 | 6.25 | 108.2 |
|   | 25 | 167.2 |
| 2 | 6.25 | 112.8 |
|   | 25 | 164.3 |
| 3 | 6.25 | 108.4 |
|   | 25 | 143.7 |

As Table 3 shows, it was found that the licorice extract compositions containing liquiritin, liquiritigenin, isoliquiritin and isoliquiritigenin but containing substantially no glycyrrhizic acid were able to effectively promote glutathione production in B16 melanoma cells.

Experimental Example 4

Test of Glutathione Production-Enhancing Activity in Hepatocytes

The glutathione production-enhancing activity of the licorice extract compositions obtained as described above (samples 1 to 3) was tested on hepatocytes as described below.

Normal human hepatocytes (Cell System-Hc Cells, by Cell Systems) were cultured using CS-C serum-free medium (by Cell Systems), after which the cells were collected by trypsinization. The collected cells were diluted with CS-C serum-free medium, to a cell density of $1.0 \times 10^5$ cells/mL. Thereafter, a 24-well plate was seeded with 400 µL of cells per well, and the cells were incubated overnight.

After incubation, 400 µL of sample solution dissolved in CS-C serum-free medium (samples 1 to 3, sample concentration as per Table 4 below) were added to each well, followed by incubation for 24 hours. Once incubation was over, the medium was removed from the wells, and each well was washed with 400 µL of PBS (−). The cells were then lysed using 250 µL of M-PER (PIERCE).

Total glutathione was quantified using 100 µL of that lysate. Specifically, a 96-well plate was charged with 100 µL of dissolved cell liquid lysate, 50 µL of a 0.1 M phosphate buffer solution, 25 µL of 2 mM NADPH, and 25 µL of glutathione reductase (final concentration 17.5 unit/mL), with warming for 10 minutes at 37° C. Next, 25 µL of 10 mM 5,5'-dithiobis (2-nitrobenzoic acid) were added, and absorbance was measured until 5 minutes thereafter at a wavelength of 412 nm, to work out ΔOD/min. The total glutathione concentration was calculated on the basis of a calibration curve plotted using oxidized glutathione (by Wako Pure Chemical). The obtained values were corrected to amount of glutathione per total protein amount, and then the glutathione production promotion rate (%) was calculated on the basis of the formula below.

Glutathione production promotion rate (%)=$B/A \times 100$

In the formula, A denotes "amount of glutathione per total protein amount in cells with no sample added (control)", and B denotes "amount of glutathione per total protein amount in cells with sample added".

The results are given in Table 4.

TABLE 4

| Sample | Sample concentration (µg/mL) | Glutathione production promotion rate (%) |
|---|---|---|
| 1 | 25 | 104.4 |
|   | 100 | 111.4 |
|   | 200 | 114.3 |
| 2 | 25 | 105.3 |
|   | 100 | 103.2 |
|   | 200 | 121.9 |
| 3 | 25 | 103.6 |
|   | 100 | 109.2 |
|   | 200 | 110.6 |

As Table 4 shows, it was found that the licorice extract compositions containing liquiritin, liquiritigenin, isoliquiritin and isoliquiritigenin but containing substantially no glycyrrhizic acid were able to effectively promote glutathione production in hepatocytes.

Experimental Example 5

Test of γ-glutamylcysteine Synthetase mRNA Expression Promotion Activity in Epidermal Keratinocytes The γ-glutamylcysteine synthetase mRNA expression promotion activity of the licorice extract compositions obtained above (samples 1 to 3) was tested on epidermal keratinocytes as follows.

Normal human epidermal keratinocytes (NHEK) were cultured using a culture medium for long-term culture of normal human epidermal keratinocytes (EpiLife-KG2), after which the cells were collected by trypsinization. The collected cells were diluted with EpiLife-KG2, to a cell density of $1.0 \times 10^5$ cells/mL, after which 35 mm Petri dishes were seeded each with 2.5 mL of the cells, which were incubated overnight.

After incubation, 2.5 mL of sample solution dissolved in EpiLife-KG2 (samples 1 to 3, sample concentration according to Table 5 below) was added, and incubation continued a further 16 hours. Once incubation was over, the culture medium was discarded and total RNA was extracted using ISOGEN (by Nippon Gene, Cat. No. 311-02501). The respective RNA amounts were measured using a spectrophotometer, and total RNA was adjusted to 200 µg/mL.

The expression level of mRNA for γ-glutamylcysteine synthetase and GAPDH, as an internal standard, were measured using the above total RNA as a template. Detection was performed by real-time 2-step RT-PCR using a TaKaRa SYBR PrimeScript™ RT-PCR Kit (Perfect Real Time, code No. RR063A), in a real-time PCR device Smart Cycler (by Cepheid). The expression level of mRNA of γ-glutamylcysteine synthetase was corrected by the expression level of mRNA of GAPDH in the same sample. Thereafter, the corrected value of "with sample added" was calculated taking 100 as the corrected value of "with no sample added". The mRNA expression promotion rate (%) of γ-glutamylcysteine synthetase was calculated on the basis of the formula below.

mRNA expression promotion rate (%)=$B/A \times 100$

In the formula, A denotes "mRNA expression level with no sample added (control)", and B denotes "mRNA expression level with sample added".

The results are given in Table 5.

TABLE 5

| Sample | Sample concentration (μg/mL) | mRNA expression promotion rate (%) |
|---|---|---|
| 1 | 6.25 | 241.2 |
|   | 25 | 891.7 |
| 2 | 6.25 | 205.6 |
|   | 25 | 638.2 |
| 3 | 6.25 | 196.1 |
|   | 25 | 487.2 |

As Table 5 shows, it was found that the licorice extract compositions containing liquiritin, liquiritigenin, isoliquiritin and isoliquiritigenin but containing substantially no glycyrrhizic acid were able to effectively promote expression of γ-glutamylcysteine synthetase mRNA in epidermal keratinocytes.

Experimental Example 6

Test of γ-glutamylcysteine Synthetase mRNA Expression Promotion Activity in Dermal Fibroblasts The γ-glutamylcysteine synthetase mRNA expression promotion activity of the licorice extract compositions obtained above (samples 1 to 3) was tested on dermal fibroblasts as described below.

Normal human dermal fibroblasts (NB1RGB) were cultured using a 10% FBS-containing α-MEM, after which the cells were collected by trypsinization. The collected cells were diluted with 10% FBS-containing α-MEM down to a cell density of $2.0 \times 10^5$ cells/mL, after which 35 mm Petri dishes were seeded each with 2.5 mL of the cells, which were incubated overnight.

After incubation, 2.5 mL of sample solution dissolved in 1% FBS-containing D-MEM (samples 1 to 3, sample concentration according to Table 6 below) was added, and incubation continued a further 16 hours. Once incubation was over, the culture medium was discarded and total RNA was extracted using ISOGEN (by Nippon Gene, Cat. No. 311-02501). The respective RNA amounts were measured using a spectrophotometer, and total RNA was adjusted to 200 μg/mL.

The expression level of mRNA for γ-glutamylcysteine synthetase and GAPDH, as an internal standard, were measured using the above total RNA as a template. Detection was performed by real-time 2-step RT-PCR using a TaKaRa SYBR PrimeScript™ RT-PCR Kit (Perfect Real Time, code No. RR063A), in a real-time PCR device Smart Cycler (by Cepheid). The expression level of mRNA of γ-glutamylcysteine synthetase was corrected by the expression level of mRNA of GAPDH in the same sample. Thereafter, the corrected value of "with sample added" was calculated taking 100 as the corrected value of "with no sample added". The mRNA expression promotion rate (%) of γ-glutamylcysteine synthetase was calculated on the basis of the formula below.

mRNA expression promotion rate (%)=$B/A \times 100$

In the formula, A denotes "mRNA expression level with no sample added (control)", and B denotes "mRNA expression level with sample added".

The results are given in Table 6.

TABLE 6

| Sample | Sample concentration (μg/mL) | mRNA expression promotion rate (%) |
|---|---|---|
| 1 | 25 | 122.3 |
| 2 |   | 162.6 |
| 3 |   | 139.4 |

As Table 6 shows, it was found that the licorice extract compositions containing liquiritin, liquiritigenin, isoliquiritin and isoliquiritigenin but containing substantially no glycyrrhizic acid were able to effectively promote expression of γ-glutamylcysteine synthetase mRNA in dermal fibroblasts.

Experimental Example 7

Test of γ-glutamylcysteine Synthetase mRNA Expression Promotion Activity in B16 Melanoma Cells The γ-glutamylcysteine synthetase mRNA expression promotion activity of the licorice extract compositions obtained above (samples 1 to 3) was tested on B16 melanoma cells as described below.

B16 melanoma cells were cultured using 10% FBS-containing D-MEM medium, after which the cells were collected by trypsinization. The collected cells were diluted with 10% FBS-containing D-MEM, to a cell density of $1.0 \times 10^5$ cells/mL, after which 35 mm Petri dishes were seeded each with 2.5 mL of the cells, which were incubated overnight.

After incubation, 2.5 mL of sample solution dissolved in 1% FBS-containing D-MEM medium (samples 1 to 3, sample concentration according to Table 7 below) was added, and incubation continued a further 16 hours. Once incubation was over, the culture medium was discarded and total RNA was extracted using ISOGEN (by Nippon Gene, Cat. No. 311-02501). The respective RNA amounts were measured using a spectrophotometer, and total RNA was adjusted to 100 μg/mL.

The expression level of mRNA for γ-glutamylcysteine synthetase and GAPDH, as an internal standard, were measured using the above total RNA as a template. Detection was performed by real-time 2-step RT-PCR using a TaKaRa SYBR PrimeScript™ RT-PCR Kit (Perfect Real Time, code No. RR063A), in a real-time PCR device Smart Cycler (by Cepheid). The expression level of mRNA of γ-glutamylcysteine synthetase was corrected by the expression level of mRNA of GAPDH in the same sample. Thereafter, the corrected value of "with sample added" was calculated taking 100 as the corrected value of "with no sample added". The mRNA expression promotion rate (%) of γ-glutamylcysteine synthetase was calculated on the basis of the formula below.

mRNA expression promotion rate (%)=$B/A \times 100$

In the formula, A denotes "mRNA expression level with no sample added (control)", and B denotes "mRNA expression level with sample added".

The results are given in Table 7.

TABLE 7

| Sample | Sample concentration (μg/mL) | mRNA expression promotion rate (%) |
|---|---|---|
| 1 | 25 | 140.3 |
| 2 | | 165.7 |
| 3 | | 132.8 |

As Table 7 shows, it was found that the licorice extract compositions containing liquiritin, liquiritigenin, isoliquiritin and isoliquiritigenin but containing substantially no glycyrrhizic acid were able to effectively promote expression of γ-glutamylcysteine synthetase mRNA in B16 melanoma cells.

Experimental Example 8

Test of γ-glutamylcysteine Synthetase mRNA Expression Promotion Activity in Hepatocytes The γ-glutamylcysteine synthetase mRNA expression promotion activity of the licorice extract compositions obtained above (samples 1 to 3) was tested on hepatocytes as described below.

Normal human hepatocytes (Cell System-Hc Cells, by Cell Systems) were cultured using CS-C serum-free medium (by Cell Systems), after which the cells were collected by trypsinization. The collected cells were diluted with CS-C serum-free medium, to a cell density of $1.0 \times 10^5$ cells/mL, after which 35 mm Petri dishes were seeded each with 2.5 mL of the cells, which were incubated overnight.

After incubation, 2.5 mL of sample solution dissolved in CS-C serum-free medium (samples 1 to 3, sample concentration according to Table 8 below) was added, and incubation continued a further 16 hours. Once incubation was over, the culture medium was discarded and total RNA was extracted using ISOGEN (by Nippon Gene, Cat. No. 311-02501). The respective RNA amounts were measured using a spectrophotometer, and total RNA was adjusted to 200 μg/mL.

The expression level of mRNA for γ-glutamylcysteine synthetase and GAPDH, as an internal standard, were measured using the above total RNA as a template. Detection was performed by real-time 2-step RT-PCR using a TaKaRa SYBR PrimeScript™ RT-PCR Kit (Perfect Real Time, code No. RR063A), in a real-time PCR device Smart Cycler (by Cepheid). The expression level of mRNA of γ-glutamylcysteine synthetase was corrected by the expression level of mRNA of GAPDH in the same sample. Thereafter, the corrected value of "with sample added" was calculated taking 100 as the corrected value of "with no sample added". The mRNA expression promotion rate (%) of γ-glutamylcysteine synthetase was calculated on the basis of the formula below.

mRNA expression promotion rate (%)=$B/A \times 100$

In the formula, A denotes "mRNA expression level with no sample added (control)", and B denotes "mRNA expression level with sample added".

The results are given in Table 8.

TABLE 8

| Sample | Sample concentration (μg/mL) | mRNA expression promotion rate (%) |
|---|---|---|
| 1 | 50 | 110.5 |
| 2 | | 138.6 |
| 3 | | 118.2 |

As Table 8 shows, it was found that the licorice extract compositions containing liquiritin, liquiritigenin, isoliquiritin and isoliquiritigenin but containing substantially no glycyrrhizic acid were able to effectively promote expression of γ-glutamylcysteine synthetase mRNA in hepatocytes.

The above-described Experimental examples 1 to 4 show that the licorice extract compositions containing liquiritin, liquiritigenin, isoliquiritin and isoliquiritigenin but containing substantially no glycyrrhizic acid have excellent glutathione production-enhancing activity. Also, Experimental examples 5 to 8 show that the licorice extract compositions containing liquiritin, liquiritigenin, isoliquiritin and isoliquiritigenin but containing substantially no glycyrrhizic acid have excellent γ-glutamylcysteine synthetase mRNA expression promotion activity. These indicate that, thanks to the γ-glutamylcysteine synthetase mRNA expression promotion activity, the licorice extract compositions containing liquiritin, liquiritigenin, isoliquiritin and isoliquiritigenin but containing substantially no glycyrrhizic acid promote the biosynthesis of γ-glutamylcysteine, which is a glutathione precursor, and promote as a result in-vivo production of glutathione.

Experimental Example 9

Measurement of the Amount of Glutathione in Farmed Fish

There was measured the amount of glutathione in muscle tissue of fished farmed under the conditions below, using the licorice extract composition (sample 1) obtained in Preparation example 1 as a fish-farming feed.

| | | |
|---|---|---|
| (1) | Test fish: | farmed red seabream averaging 1 kg |
| (2) | Test period: | September to October |
| (3) | No. of fish tested: | 10/6000 (free fish) |
| (4) | Administration amount: 20 mg of sample 1/kg fish weight | |
| (5) | Administration method: feeding for 4 days, 3 days rest (over one month) | |
| (6) | Measurement date: one month after start of the test | |

The amount of glutathione in muscle tissue of farmed fish was measured as follows.

Muscle (back) of farmed red seabream in the administration group of sample 1 was homogenized with 5% 5-sulfosalicylic acid, and was then centrifuged at 4° C. The supernatant was used as the sample solution. A 96-well plate was charged with 25 μL of the sample solution, and 125 μL of a 0.1 M phosphate buffer solution. Next, 25 μL of 10 mM 5,5'-dithiobis (2-nitrobenzoic acid) were added, and absorbance was measured until 5 minutes thereafter at a wavelength of 412 nm, to work out ΔOD/min. The reduced glutathione concentration was calculated using a calibration curve prepared using a reduced glutathione standard. In a control group, the reduced glutathione concentration was measured, in the same way, in muscle (back) of farmed red seabream grown under the same conditions as above, but without administration of sample 1.

The results are given in Table 9.

TABLE 9

|  | Glutathione amount (mg/100 g muscle) |
| --- | --- |
| Sample 1 administration group | 11.1 |
| Control group | 8.9 |

As Table 9 shows, it was found that a licorice extract composition containing liquiritin, liquiritigenin, isoliquiritin and isoliquiritigenin but containing substantially no glycyrrhizic acid had an effect of effectively increasing the amount of glutathione in muscle of farmed red seabream.

Experimental Example 10

Measurement of Amount of Glutathione in Mouse Skin

HR-1/Hos five-week-old female hairless mice (from Hoshino Laboratory Animals) were acclimatized for one week, and were then fed a mixture of licorice extract composition (sample 1) obtained in Preparation example 1 and a powder sample (Labo-MR stock, by Shimizu Laboratory Supplies). Feeding continued daily for three weeks at a daily ingestion amount of licorice extract composition (sample 1) of 50 (mg/kg of mouse body weight). Once feeding was over, the skin was sampled and was solubilized, using a Teflon homogenizer, in 100 μL of PBS containing 1% of TritonX-100, per 1 mg of skin, and was centrifuged at 4° C. (12000 rpm, 15 min). The supernatant was used as the measurement sample.

Total glutathione was determined using 25 μL from the obtained measurement sample. Specifically, a 96-well plate was charged with 25 μL of measurement sample, 125 μL of a 0.1 M phosphate buffer solution, 25 μL of 2 mM NADPH, and 25 μL of glutathione reductase (final concentration: 17.5 unit/mL), with warming for 10 minutes at 37° C. Next, 25 μL of 10 mM 5,5'-dithiobis (2-nitrobenzoic acid) were added, and absorbance was measured until 5 minutes thereafter at a wavelength of 412 nm, to work out ΔOD/min. The total glutathione concentration was calculated, as the amount of glutathione per weight of skin, from a value calculated on the basis of a calibration curve plotted using oxidized glutathione (by Wako Pure Chemical). In a control group, the total glutathione concentration in mouse skin was calculated in the same way as above, but without addition of licorice extract composition (sample 1) to the powder feed.

The results are given in Table 10.

TABLE 10

|  | Glutathione amount (mg/100 g skin) |
| --- | --- |
| Sample 1 administration group | 38.0 |
| Control group | 23.6 |

As Table 10 shows, it was found that a licorice extract composition containing liquiritin, liquiritigenin, isoliquiritin and isoliquiritigenin but containing substantially no glycyrrhizic acid had an effect of effectively increasing the amount of glutathione in mouse skin.

Blending Example 1

A mixed feed having the composition below was prepared in accordance with ordinary methods.

Licorice Extract Composition

| (Preparation example 1) | 1 wt % |
| --- | --- |
| Fish meal | 75 wt % |
| Wheat flour | 10 wt % |
| Starch | 7 wt % |
| Fish oil | 3 wt % |
| Minerals | 2 wt % |
| Vitamins | 2 wt % |

Blending Example 2

Tablets having the composition below were prepared in accordance with ordinary methods.

Licorice Extract Composition

| (Preparation example 1) | 30.0 mg |
| --- | --- |
| Whey minerals (containing 25 to 30% calcium) | 100.0 mg |
| Vitamin $K_2$ (1% powder) | 1.5 mg |
| Maltitol | 156.0 mg |
| Glycerin fatty acid ester | 12.5 mg |

Blending Example 3

Tablets having the composition below were prepared in accordance with ordinary methods.

Licorice Extract Composition

| (Preparation example 2) | 15.0 mg |
| --- | --- |
| Dolomite (calcium 20%, magnesium 10%) | 83.4 mg |
| Casein phosphopeptide | 16.7 mg |
| Vitamin C | 33.4 mg |
| Maltitol | 126.8 mg |
| Collagen | 12.7 mg |
| Sucrose fatty acid ester | 12.0 mg |

Blending Example 4

Capsules having the composition below were prepared in accordance with ordinary methods. The capsules used were #1 hard gelatin capsules.

<Composition of 1 Capsule (200 mg)>

Licorice Extract Composition

| (Preparation example 2) | 20.0 mg |
| --- | --- |
| Cornstarch | 60.0 mg |
| Lactose | 100.0 mg |
| Calcium lactate | 10.0 mg |
| Hydroxypropyl cellulose (HPC-L) | 10.0 mg |

Blending Example 5

An oral liquid preparation having the composition below was prepared in accordance with ordinary methods.

<Composition of One Ampoule (100 mL)>
Licorice Extract Composition

| | |
|---|---|
| (Preparation example 3) | 0.4 wt % |
| Sorbitol | 12.0 wt % |
| Sodium benzoate | 0.1 wt % |
| Fragrance | 1.0 wt % |
| Calcium sulfate | 0.5 wt % |
| Purified water | balance |

INDUSTRIAL APPLICABILITY

The glutathione production enhancer of the present invention allows preventing, treating or improving skin aging, blemishes, damage from oxidative stress caused by ultraviolet radiation, and diseases caused by glutathione deficiency (for instance, diseases caused by oxidative stress from reactive oxygen species or the like; liver diseases such as hepatitis and liver dysfunction; chronic renal failure; respiratory diseases such as idiopathic pulmonary fibrosis or adult respiratory syndrome; cataracts; ischemic heart disease; Parkinson's disease; Alzheimer's disease; gastrointestinal diseases such as gastric ulcer; cancer; bone marrow aplasia; acquired immunodeficiency syndrome; latent viral infections and the like) and also sleeps disorders, such as insomnia, that are caused by oxidized glutathione deficiency.

The invention claimed is:

1. A method for promoting glutathione production in human cells in need of promoting glutathione production in vivo or animal cells in need of promoting glutathione production in vivo, comprising steps of:
preparing a glutathione production enhancer containing, as an active ingredient, a licorice extract composition that contains liquiritin, liquiritigenin, isoliquiritin and isoliquiritigenin, wherein dry solid content of glycyrrhizic acid in the licorice extract composition is no greater than 1.0 wt % in combination with a total combined amount of the liquiritin, liquiritigenin, isoliquiritin and isoliquiritigenin in the licorice extract composition of no less than 10.6 wt %; and
administering an effective amount of the glutathione production enhancer to a predetermined site of a human or an animal for promoting glutathione production.

2. A method for preparing a licorice extract composition that contains liquiritin, liquiritigenin, isoliquiritin and isoliquiritigenin and substantially no glycyrrhizic acid, comprising:
a first step of obtaining an initial licorice extract from a licorice, the initial licorice extract containing liquiritin, liquiritigenin, isoliquiritin, isoliquiritigenin and glycyrrhizic acid and from which the glycyrrhizic acid was not substantially removed, and
a second step of removing the glycyrrhizic acid from the initial licorice extract to obtain a solid content of glycyrrhizic acid in the licorice extract composition of no greater than 1.0 wt % in combination with a total combined amount of the liquiritin, liquiritigenin, isoliquiritin and isoliquiritigenin in the licorice extract composition of no less than 10.6 wt %.

3. A method for treating or improving skin aging or pigmentation disorders in a patient in need of treating or improving skin aging or pigmentation disorders, comprising steps of:
preparing a therapeutic agent for skin aging or pigmentation disorders containing, as an active ingredient, a licorice extract composition that contains liquiritin, liquiritigenin, isoliquiritin and isoliquiritigenin, and a dry solid content of glycyrrhizic acid of no greater than 1.0 wt % in combination with a total combined amount of the liquiritin, liquiritigenin, isoliquiritin and isoliquiritigenin in the licorice extract composition of no less than 10.6 wt %; and
administering an effective amount of the therapeutic agent to the patient for treating or improving skin aging or pigmentation disorders.

* * * * *